US00PP11875P2

(12) United States Plant Patent
Fruehwirth

(10) Patent No.: US PP11,875 P2
(45) Date of Patent: May 15, 2001

(54) POINSETTIA PLANT NAMED 'ECKABRA'

(75) Inventor: Franz Fruehwirth, Encinitas, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/432,710

(22) Filed: Nov. 2, 1999

(51) Int. Cl.[7] ..... A01H 5/00
(52) U.S. Cl. ..... Plt./307

(58) Field of Search ..... Plt./307

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Poinsettia plant named 'Eckabra', characterized by its bright red bracts; response time about 9.5 weeks; light yellow and two-tone green variegated leaves with red purple petioles; upright plant habit; and good postproduction longevity.

2 Drawing Sheets

BACKGROUND OF THE INVENTION

The present invention relates to a new and distinct cultivar of Poinsettia plant, botanically known as *Euphorbia pulcherrima* Willd., and hereinafter referred to by the name 'Eckabra'.

The new cultivar is a product of a planned breeding program conducted by the Inventor in Eucinitas, Calif. The objective of the program is to create new Poinsettia cultivars having interesting bract and leaf display, color and form; strong and freely branching stems; and good post-production longevity.

The new cultivar originated from a cross made by the Inventor of the Poinsettia cultivar '529', disclosed in U.S. Plant Pat. No. 8,371, as the female, or seed parent, with the proprietary selection identified as 587 as the male, or pollen parent.

The cultivar Eckabra was discovered and selected by the Inventor as a flowering plant within the progeny of the stated cross in a controlled environment in Eucinitas, Calif. in December, 1995.

Asexual reproduction of the new Poinsettia by terminal cuttings taken at Eucinitas, Calif, has shown that the unique features of this new Poinsettia are stable and reproduced true to type in successive generations of asexual reproduction.

BRIEF SUMMARY OF THE INVENTION

The following traits has been repeatedly observed and are determined to be the unique characteristics of 'Eckabra'. These characteristics in combination distinguish 'Eckabra' as a new and distinct cultivar:

1. Bright red bracts.

2. Response time about 9.5 weeks.

3. Light yellow and two-tone green variegated leaves with red purple petioles.

4. Upright plant habit.

5. Good postproduction longevity.

In side-by-side comparisons conducted in Eucinitias, Calif, plants of the new Poinsettia have variegated foliage and lighter red-colored bracts than plants of the female parent, the cultivar '529'. Compared to plants of the male parent, the selection 587, plants of the new Poinsettia have variegated foliage, flatter bracts and flower later.

Plants of the new Poinsettia can be compared to plants of the cultivar 'Fissilver', disclosed in U.S. Plant Pat. No. 9,989. However, in side-by-side comparisons conducted in Eucinitas, Calif, plants of the new Poinsettia differed from plants of 'Fissilver' in the following characteristics:

1. Plants of the new Poinsettia are more upright and slightly taller than plants of 'Fissilver'.

2. Leaves of the new Poinsettia have two-tone green centers surrounded by a wide light yellow margin whereas leaves of 'Fissilver' have light green centers surrounded by a narrow whitish green margin.

3. Plants of the new Poinsettia flower later than plants of 'Fissilver'.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type.

The photograph at the top of the first sheet comprises a side perspective view of a typical plant of 'Eckabra'.

The photograph at the bottom of the first sheet comprises a top perspective view of a typical plant of 'Eckabra'.

The photograph on the second sheet is a close-up view of typical bracts and leaves of 'Eckabra' (left) and 'Fissilver' (right). Bract and foliage colors in the photographs may differ from actual colors due to light reference.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Eucinitas, Calif, under commercial practice in a glass-covered greenhouse with day temperatures ranging from 21 to 27° C., night temperature ranging from 18 to 20° C., and light levels about 4,000 foot-candles. Plants were grown in 16-cm pots, pinched one time, and flowered under naturally lengthening nights during the fall/early winter.

In the following description, color references are made to The Royal Horticultural Society Colour Chart except where general terms of ordinary dictionary significance are used.

Botanical classification: *Euphorbia pulcherrima* Willd. 'Eckabra'.

Parentage:

*Female parent.*—*Euphorbia pulcherrima* Willd. '529', disclosed in U.S. Plant Pat. No. 8,371.

*Male parent.*—Proprietary selection of *Euphorbia pulcherrima* Willd. indentified of 587.

Propagation:

*Type cutting.*—Terminal cuttings.

*Time to initiate roots.*—Summer: About 7 days at 24° C. Winter: About 10 days at 22° C.

*Time to develop roots.*—Summer: About 26 days at 24° C. Winter: About 26 days at 22° C.

*Rooting habit.*—Freely branching, becoming fibrous with development.

Plant description:

*Plant from.*—Inverted triangle.

*Growth habit.*—Very upright. Branching in enhanced by removing the shoot apex.

*Plant vigor.*—Moderate.

*Plant height.*—About 28 cm.

*Crop time.*—From unrooted cuttings to a flowering plant in a 16-cm container, about 18 weeks are required.

*Stem description.*—Number of lateral branches: About five lateral branches are formed after removal of the terminal apex. Lateral branch length: About 21.5 cm. Internode length: About 1.5 cm. Stem color: 146A.

*Foliage description.*—Quantity of leaves per lateral branch: About 8. Length: About 10.2 cm. Width: About 7 cm. Shape: Mostly ovate, occasionally lobed. Apex: Acuminate. Base: Acute. Margin: Entire. Texture: Smooth, velvety; very sparse pubescense on lower surface. Color: Two-tone green centers surrounded by light yellow margins; irregular variegation patterns. Young foliage, upper surface: Center, 147B and 147C; margin, 11C. Young foliage, lower surface: Center, 138A; margin 11C. Mature foliage, upper surface: Center, 137C and 148B; margin, 11A. Mature foliage, lower surface: Center, 138B; margin, 11B. Venation, upper surface: 145B. Venation, lower surface: 147C. Petiole: Length: About 5.25 cm. Diameter: About 2 mm. Color: 59A.

*Inflorescence description:*

*Inflorescence type and habit.*—Inflorescenses are compound corymbs of cyathia with colored flower bracts subtending the cyathia.

*Natural flowering season.*—Autumn/winter in Northern Hemisphere. Flower initiation and development can be induced under long night conditions. Response time is about 9.5 weeks.

*Quantity of inflorescences.*—One per lateral branch, usually about five per plant.

*Inflorescence size.*—Diameter: About 22 cm. Height (depth): About 3.5 cm.

*Flower bracts.*—Quantity of flower bracts per inflorescence: Usually about 15 primary bracts and about 6 smaller secondary bracts per inflorescence. Length, largest bracts: About 10.5 cm. Width, largest bracts: About 6 cm. Shape: Mostly ovate, occasional irregularly lobed. Apex: Acuminate. Base: Acute. Margin: Entire. Texture: Smooth, velvety. Aspect: Held mostly horizontal. Color: Developing, upper surface: Brighter than 46A. Developing, lower surface: 46D. Mature, upper surface: 45A. Mature, lower surface: 47B to 47C.

*Cyathia.*—Quantity: Usually about 16 per corymb. Diameter of cyathia cluster: About 2.5 by 3 cm. Length: About 1 cm. Width: About 8 mm. Color: Immature: 144B. Mature: 144C. Peduncle: Length: About 4 mm. Aspect: Strong, erect. Color: 144C. Stamens: Stamen number: Numerous, usually more than 20 with many stamenodes per cyathium. Anther length: About 1 mm. Anther shape: Oval. Anther color: 45A. Amount of pollen: Scarce. Pollen color: 4A. Pistils: No pistillate flowers observed. Nectary color: 4B to 13A.

*Disease resistance*: Plants of the new Poinsettia have not been observed to be resistant to pathogens common to Poinsettias.

*Postproduction longevity*: Good; generally plants maintain good substance and bract color for about six to eight weeks under interior conditions.

It is claimed:

1. A new and distinct cultivar of Poinsettia plant named 'Eckabra', as illustrated and described.

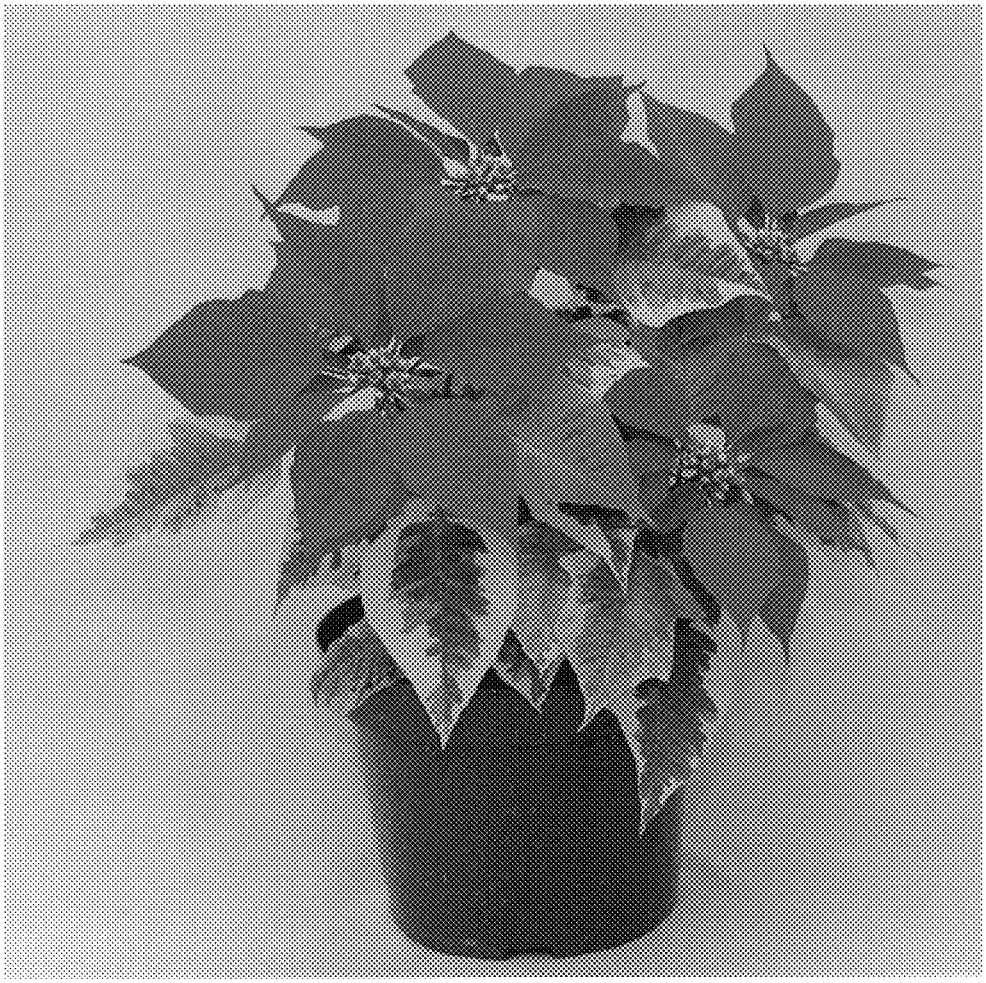
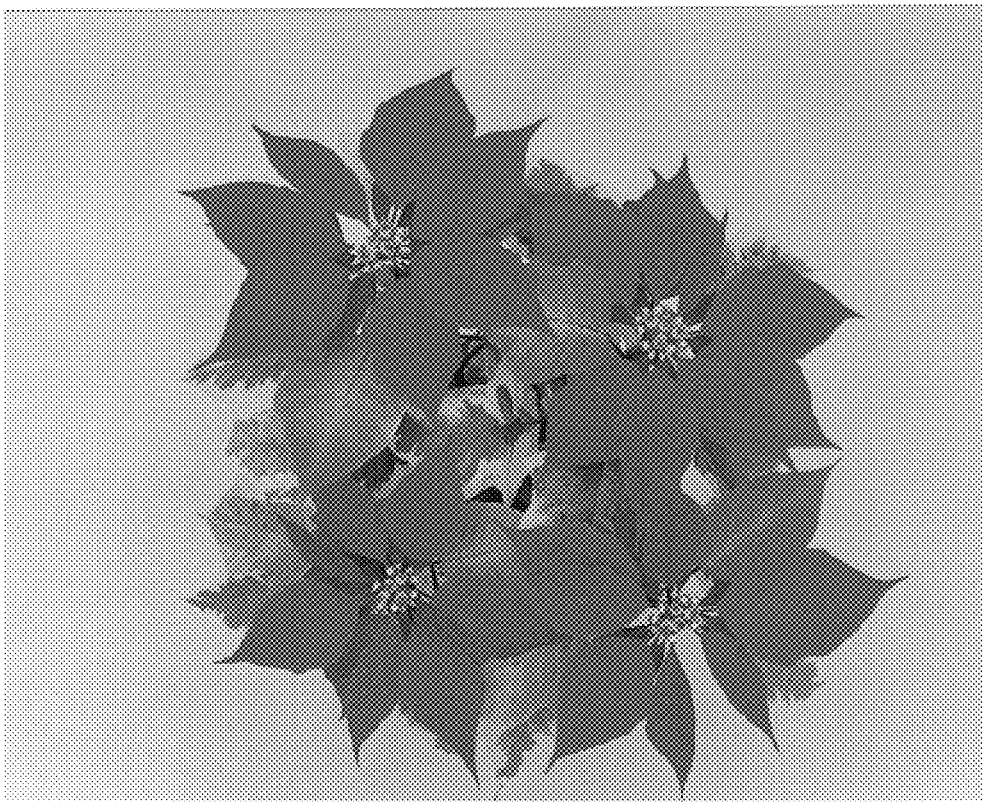

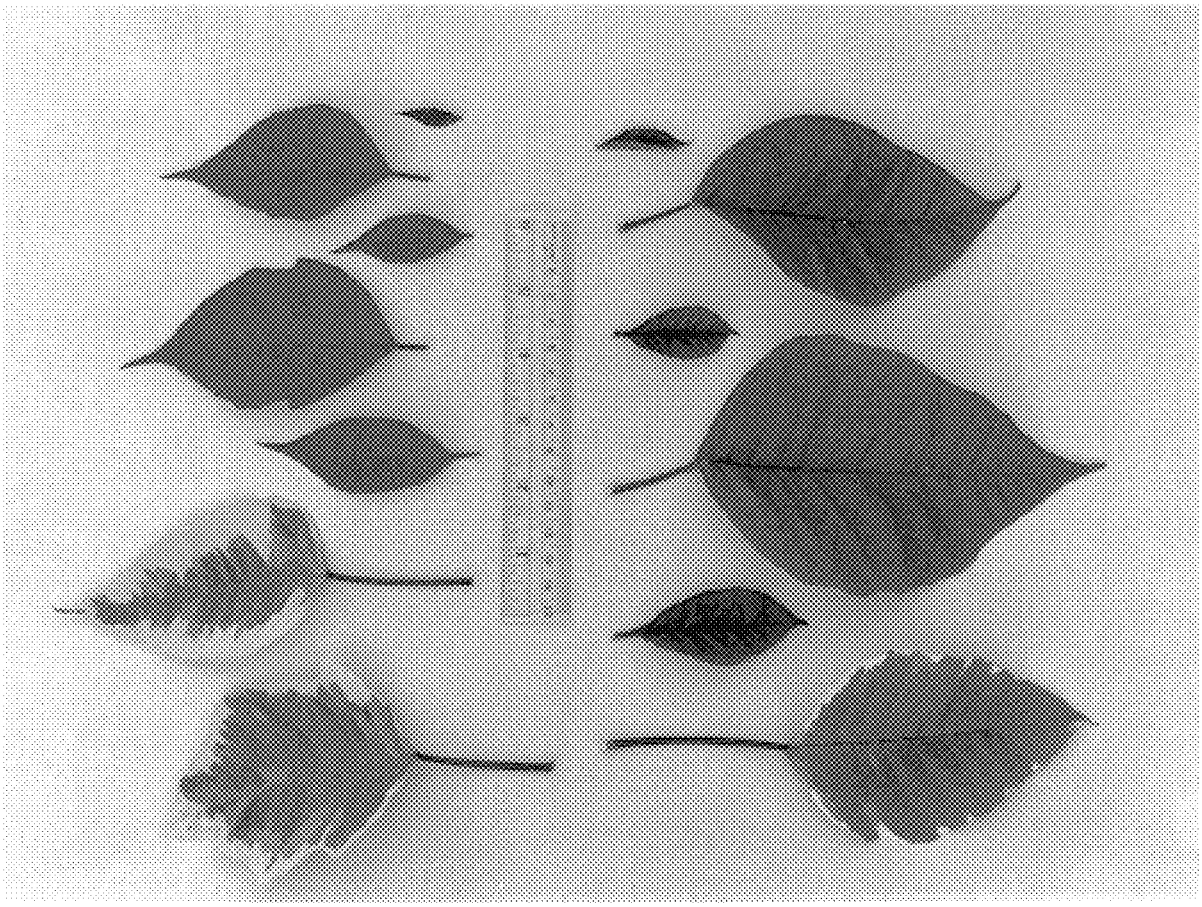

* * * * *